United States Patent [19]

Liau

[11] 4,273,758

[45] Jun. 16, 1981

[54] DENTIFRICE AND ITS METHOD OF MANUFACTURE

[76] Inventor: Weilin Liau, 73-9,, Aza-Honmachi, Utashinai-shi, Hokkaido, Japan, 073-04

[21] Appl. No.: 91,817

[22] Filed: Nov. 6, 1979

[51] Int. Cl.³ .............................................. A61K 7/16
[52] U.S. Cl. ...................................................... 424/49
[58] Field of Search ...................................... 424/49–58

[56] References Cited

U.S. PATENT DOCUMENTS

| 50,578 | 10/1865 | Hamilton | 424/49 |
|---|---|---|---|
| 4,146,606 | 3/1979 | Yamaga et al. | 424/49 |

FOREIGN PATENT DOCUMENTS

| 649902 | 7/1934 | Fed. Rep. of Germany | 424/58 |
|---|---|---|---|
| 2657896 | 7/1978 | Fed. Rep. of Germany | 424/58 |

*Primary Examiner*—Shep K. Rose
*Attorney, Agent, or Firm*—Wenderoth, Lind & Ponack

[57] ABSTRACT

The present invention relates to dentifrice and its method of manufacture whereby the dentifrice containing tannic acid efficacious for the prevention of outbreak of tooth decay, pyorrhea and gingivitis can be obtained by means by adding what is obtainable through adding tannic acid to hot water whereto glycerine is added after it has become cooled down to the materials for the dentifrice and mixing them together.

2 Claims, 1 Drawing Figure

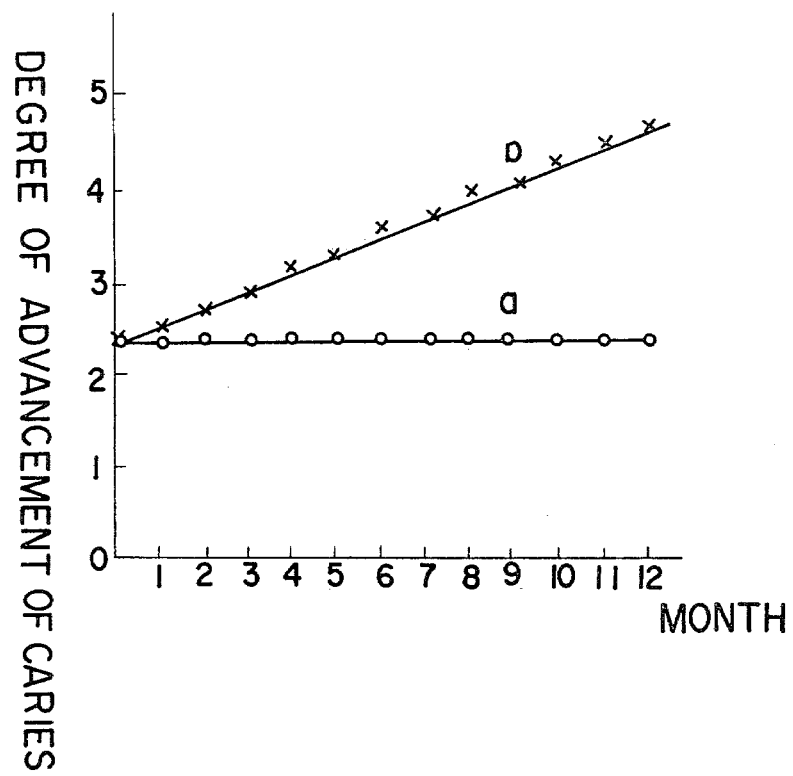

DENTIFRICE AND ITS METHOD OF MANUFACTURE

BACKGROUND OF THE INVENTION

The present invention relates to dentifrice containing tannic acid efficacious for the prevention of tooth decay, pyorrhea and gingivitis and to its method of manufacture.

In the field of dental treatment, various studies are being made of late of making oral medicines or dentifrice containing fluorides with the object of preventing or decreasing prevalence of tooth decay in the knowledge that the average rate of outbreak of patients suffering from tooth decay is comparatively lower for those who live in the regions where fluorine is contained in the drinking water in the form of fluorides in a period when their teeth are coming into being and are growing. However, the fact is that the number of patients suffering from tooth decay is increasing year by year in every country of the world and it is a question to what extent the oral medicines and dentifrice containing fluorides respectively are efficacious for the prevention of tooth decay.

Let us examine here the influence of fluorine upon the human body. Fluorine itself is one of the inorganic micro-elements in the human body and principally exists in the enamel of a tooth as well as in cartilage, skin, blood etc. The function of fluorine in the human body, however, remains unexplained. When ordinary drinking water in a region contains 2.7-5 ppm of fluorine, the region is called a fluorine region and this amount of fluorine may cause mottled tooth. It is regarded that a fluorine content of 1-2 ppm in the case of infants in particular and that of 0.8 ppm in the case of milk teeth may bring about a danger of outbreak of mottled tooth. On the other hand, as the flurine content in a decayed tooth is 0.0069% which is less than that of 0.0111% in a healthy tooth, it is considered that about 0.7 ppm of fluorine content in the drinking water is efficacious for the prevention of outbreak of tooth decay. But this amount alone does not make a perfect dental medicine against tooth decay. However, as a preventive measure against tooth decay in general, there are such methods as adding a little amount of fluorine to drinking water, application and addition of soda fluoride to dentifrice. Of the above, the addition of fluorine to drinking water is the most efficacious when it is conducted at the time when the teeth absorb calcium, or from the 4th month of pregnancy to one year in the case of milk teeth and before the age of 7 or 8 in the case of permanent teeth. Accordingly, the method of applying soda fluoride is the most efficacious when it is conducted before they cut their milk teeth and permanent teeth. Though fluorine has a function of reinforcing a formative substance of teeth as mentioned above, however, it has no function to kill bacilli. It is therefore impossible to remove causes of tooth decay only with fluorine and the application of fluorine is of no use when caries is already in an advanced stage. However, as mentioned above, water containing a soluble inorganic fluoride is efficacious for the prevention of caries and, making use of this property, various trials are made of adding soluble fluoric inorganics producing fluorine ion to dentifrice to put them to some use for the prevention of tooth decay.

As for such a soluble inorganic fluoride producing fluoric ion, it must be a substance which does no harm to the mucous membrane of the mouth, and the kinds are accordingly limited and only the fluoride of alkali metal such as soda fluoride, silicofluoride of the group of alkaline earths and tin fluoride or aluminum fluoride etc. are used under the existing circumstances. However, in the case of a dentifrice, when a soluble inorganic is added to such bases as calcium carbonate and calcium phosphate, ion dissociation takes place affected by the water contained in the dentifrice and the dissociated ion joins with calcium to become insoluble calcium fluoride resulting in eduction and, as this cannot penetrate into the tooth canaliculi, the prevention of tooth decay by fluorine ion proves inefficacious in practice. The reason why resin has come to be used as a material for dentifrice seems to lie in the fact that it does not contain polyvalent metallic ion. In spite of many efforts which have been exerted for the past tens of years to find out any satisfactory preventive medicine containing fluorine, nothing has so far been discovered which can satisfactorily be used by both dental surgeons and people in general. The fact that these sorts of dentifrice contain fluoric ions in the form which is difficult to be utilized seems to be the reason why they are not used with satisfaction as mentioned above.

SUMMARY OF THE INVENTION

The present invention has been made for solving the aforesaid questions and the object of the invention is to offer a new medicine for cleaning teeth efficacious for the prevention of tooth decay as well its method of manufacture.

One of the features of the present invention is characterized by the fact that the dentifrice has, as one of its materials, tannic acid as an additive.

Another feature of the present invention is characterized by the fact that, in its method of manufacture, hot water is added to tannic acid and then it is added to the materials for the dentifrice with glycerine added after it has cooled down and is mixed together.

BRIEF DESCRIPTION OF THE DRAWING

FIG. 1 is a graphic chart showing the experimental effects of the dentifrice according to the present invention.

DETAILED DESCRIPTION OF THE INVENTION

This inventor has for many years conducted clinical demonstrations and experiments toward the objects of investigation and has, as a result, discovered the fact that tannic acid which is the principal ingredient of tea is remarkably efficacious for the prevention and treatment of tooth decay and has an intention of utilizing the achievement for a medicine for cleaning teeth. In the aforesaid experiments, this inventor soaked tampons in 5% tannic acid and filled up cavities of decayed teeth of 2-3 degrees with them which were sealed with the stoppings, exchanged them for new ones every 3 days, removed the stoppings to uncover the teeth after exchanges 10 times and investigated the teeth every month for 12 months to find that the affected teeth had remained unchanged at 2-3 degrees of caries just the same as the decayed teeth were treated. On the other hand, the teeth of the objects of investigation which had not been filled with tannic acid, crowns of teeth had crumbled and only the roots of teeth were left behind. FIG. 1 is a comparative diagram showing the relations between the degrees of advancement of caries and the month for 10 patients who had undergone instillation of tannic acid (a) and those who had not undergone the same (b).

In the diagram, the horizontal axis shows the lapse of month and the interval of instillation conducted (a) is 3 days. As for the instillation, a tampon as big as a grain of rice which is the same size as that for general dental treatment was soaked by tannic acid, 2 or 3 drops in principle, and was inserted into the cavity of a decayed tooth to which the stopping was put. The numerical value of the degree of advancement of carries shown on the vertical axis is normally up to 4 degrees and this is universally accepted. That is to say, 1 degree of caries (indicated as $C_1$ normally) is the case where the enamel has been decayed, 2 degrees of caries ($C_2$) is the case where the decay has advanced up to the cement, 3 degrees of caries ($C_3$) is the case where the decay has advanced into the dentine and 4 degrees of caries is the case where the crown of a tooth has been decayed with only the root of a tooth remaining unaffected. Thus the advancement of caries is bigger as the number of degrees becomes bigger.

As tannic acid proves excellently efficacious clinically as mentioned above, it plays the role similar to that of vaccine when it is mixed with the base of dentifrice and is employed for a long time thus controlling the advancement of degree of caries of a decayed tooth. Tannic acid has affinity toward lactic acid and has astringent effects immediately after it has permeated capillaries and has settled there. Basically, the pH value of tannic acid at the final formative stage of dentifrice must be less than pH 5 so that excessive acid may not hurt teeth. But experiments show that tannic acid does not harm teeth also when it is lower than pH 5. The pH value of 1% tannic acid (according to the Mohs hardness measurement) is 4.4 and that of 2% tannic acid is 3.4. It is however possible on manufacturing dentifrice to hold the value so that it may become ph 5-7 by means of adding alkaline detergent in order to prevent interference of alien acid. Accordingly, when tannic acid is mixed with the base of dentifrice and is used for a long time, it is astringed and settles whereby we can get the same effects as those at the time of instillation of 5% tannic acid into a cavity of a decayed tooth conducted in the experiments as mentioned above. The Table below shows the experimental values when this inventor has checked the effectiveness of gargling with 1% tannic acid against pyorrhea and gingivitis.

In the table, the frequency of garglings is about several times a day. And "Efficacious", "Not quite efficacious" and "Inefficacious" are distinguished in the following way.

As to pyorrhea and gingivitis, specialists can tell their symptoms and the effects of treatment at once with the naked eye or when they touch them. However, when these are to be indicated in numerical values, there is such an easy way of telling the symptoms as checking up the degrees of forming bubbles at the time when the affected part was cleaned with oxydole besides taking measurement of the amount of pus coming out of the diverticula of alveoli. When much bubbles are formed, the conditions are worsened and when bubbles are not formed, it means that the affected part has been cured. In other words, when a great amount of bubbles are formed against one drop of oxydole, the treatment conducted remains "inefficacious", when bubbles are formed in medium, the treatment proves "not quite efficacious" and, finally, when bubbles are not formed at all, the treatment is meant to have been "efficacious".

(TABLE)

| Number of days of gargling | Number of people who gargled | Efficacious | Not quite efficacious | Inefficacious |
|---|---|---|---|---|
| 2 | 18 | 2 | 4 | 12 |
| 3 | 18 | 4 | 9 | 5 |
| 4 | 18 | 13 | 3 | 2 |
| 5 | 18 | 16 | 1 | 1 |
| 6 | 18 | 17 | 0 | 1 |

As another example, this inventor achieved a good result from the experiment of garglings with tannic acid with 2400 school children as objects. A good result was also observed as to the prevention of tooth decay of milk teeth.

Although the present experiments were chiefly made on school children, the same effectiveness is also expected to be obtainable from adults.

Now, the following requisites may be pointed out as important as an additive effective for the prevention of tooth decay.

(1) It must have the property of settling and also the action of strengthening teeth by means of hardening the enamel.

(2) It must have a sterilizing power against the depth of a decayed tooth and also astringency.

(3) It must have anti-destructive acidity and yet it must have affinity.

(4) It must have restraint against enzyme.

(5) As for pH, it must have at least pH 5-7 around the neutrality.

(6) It does not contain polyvalent metallic ion and yet it does not dissociate ion from the water contained in dentifrice.

(7) It must hold dentifrice base stable, make salivation active under use and does not do any harm to the membrane of the mouth.

(8) It must have a strong affinity with high molecular substances of the base and aromatics.

(9) It does not deteriorate even when it touches a tube, metallic surface of tin etc. and does not exert any effect on metal either.

It is clear that tannic acid has properties which can satisfy all the requisites mentioned above.

And tannic acid is extremely distinguished in respects of: (1) it is above all superior in its harmlessness as compared with fluorine, (2) it has no time limit for effectiveness as compared with fluorine, or, in other words, it can be used without limitation, (3) it does not do any harm to teeth even it is below pH 7 and (4) it is excellent in efficacy against tooth decay, pyorrhea and gingivitis. It is therefore possible to make a medicine for cleaning teeth at which we set the goal by means of adding tannic acid in the base of dentifrice.

EXAMPLE 1

Example of manufacture of powdered dentifrice

This inventor obtained the powdered dentifrice which was his object by means of solving 2 g. of tannic acid in 4 cc. of hot water, adding, after it has cooled down, 5 g. of glycerine, putting it, while mixing uniformly, into 0.29 g. of menthol solved with 1 cc. of ethyl, followed by putting 0.1 g. of soluble saccharin, 10 cc. of 2% boric acid, 0.01 g. of coloring matter and 1.5 g. of aromatic into it while mixing them uniformly, and then adding 50 g. of precipitating calcium carbonate, 1 g. of lauryl sulfate of soda and 3 g. of medicated soap to it followed by mixing them uniformly.

EXAMPLE 2

Example of manufacture of pasty dentifrice

This inventor succeeded in obtaining the toothpaste which was his object by means of dissolving 2 g. of tannic acid in 33 cc. of hot water, adding, after it has cooled down, 35 g. of glycerine, putting it into 0.29 g. of menthol dissolved in 1 cc. of ethyl followed by adding soluble saccharine, 10 cc. of boric acid (2%), 0.005 g. of coloring matter and 1.5 g. of aromatic to the above, followed by, while mixing them, adding 50 g. of precipitating calcium carbonate, 5 g. of magnesium carbonate, 1 g. of lauryl sulfate of soda, 5 g. of starch, 3 g. of medicated soap and mixing them evenly.

I claim:

1. A method for the manufacture of a dentifrice composition which comprises adding tannic acid to hot water, cooling the mixture, adding glycerine to the cooled mixture, adding the remaining essential ingredients for a dentifrice composition and mixing.

2. A dentifrice composition produced in accordance with the method of claim 1.

* * * * *